US008178737B2

(12) United States Patent
Leyshon

(10) Patent No.: US 8,178,737 B2
(45) Date of Patent: May 15, 2012

(54) PROPYLENE PRODUCTION

(75) Inventor: David W. Leyshon, West Chester, PA (US)

(73) Assignee: Lyondell Chemical Technology, L.P., Houston, TX (US)

( * ) Notice: Subject to any disclaimer, the term of this patent is extended or adjusted under 35 U.S.C. 154(b) by 883 days.

(21) Appl. No.: 11/818,318

(22) Filed: Jun. 14, 2007

(65) Prior Publication Data

US 2008/0312481 A1 Dec. 18, 2008

(51) Int. Cl.
*C07C 6/04* (2006.01)
*C07C 5/25* (2006.01)

(52) U.S. Cl. ......... 585/328; 585/332; 585/643; 585/664

(58) Field of Classification Search .................. 585/328, 585/332, 643, 664
See application file for complete search history.

(56) References Cited

U.S. PATENT DOCUMENTS 3,326,866 A * 6/1967 Haag ............................ 585/458
3,531,545 A 9/1970 Garner et al.
4,242,530 A 12/1980 Smith, Jr.
4,515,661 A * 5/1985 Ogura et al. .................... 203/60
4,992,612 A 2/1991 Suzukamo et al.
4,992,613 A 2/1991 Brownscombe
5,120,894 A 6/1992 McCauley
5,153,165 A 10/1992 Lowery et al.
5,288,370 A 2/1994 Asselineau et al.
5,300,718 A * 4/1994 McCaulley .................. 585/324
5,898,091 A 4/1999 Chodorge et al.
6,333,442 B1 * 12/2001 Cosyns et al. ................ 585/332
6,586,649 B1 7/2003 Botha et al.
2003/0004385 A1 1/2003 Gartside et al.
2004/0077909 A1 4/2004 Commereuc et al.
2004/0249229 A1 12/2004 Gee et al.
2005/0154246 A1 7/2005 Adrian et al.
2006/0084831 A1 4/2006 Zhang
2006/0089517 A1 4/2006 Podrebarac et al.
2006/0161033 A1 7/2006 Chodorge et al.

FOREIGN PATENT DOCUMENTS

EP 0 079 679 5/1983

OTHER PUBLICATIONS

N. Calamur et al., "Butylenes", Kirk-Othmer Encyclopedia of Chemical Technology, online edition (2007), vol. 4, p. 402.
R. Banks, "Olefin Metathesis: Technology and Application", Appl. Ind. Catal., (1984), vol. 3, p. 215.
A. J. DeRosset et al., "Symposium on recent advances in the production and utilization of light olefins", Prepr.—Am. Chem. Soc., Div. Pet. Chem., (1978), vol. 23(2), p. 766.
J. H. Gregor, "Fischer-Tropsch Products as Liquid Fuels or Chemicals", Calal. Lett., (1990), vol. 7(1-4), p. 317.
A. E. Eleazar et al., "Hydro-isomerization of C4s", Hydrocarbon Process., Int., Ed., (May 1979), p. 112.

* cited by examiner

*Primary Examiner* — Thuan Dinh Dang

(57) ABSTRACT

A process for producing propylene from ethylene and a feed stream comprising 1-butene, 2-butene, n-butane, and isobutane is disclosed. A butenes stream (1-butene and 2-butene) is produced from the feed stream by removing the paraffins. The butenes stream is reacted in the presence of an isomerization catalyst to produce an isomerized stream with increased concentration of 2-butene. The isomerized stream is reacted with ethylene in the presence of a metathesis catalyst to produce a reaction mixture comprising propylene; the propylene may be isolated from the reaction mixture by distillation. The removal of paraffins from the feed stream improves the catalyst productivity and the plant throughput.

20 Claims, 1 Drawing Sheet

1
2
3
4
5
6
7
8
9
10
11
12
13
14
15
16
17
18
19
20
21
22
23
24
25
26

PROPYLENE PRODUCTION

FIELD OF THE INVENTION

The invention relates to a process for producing propylene from ethylene and a feed stream comprising 1-butene, 2-butene, isobutane, and n-butane.

BACKGROUND OF THE INVENTION

Mixed $C_4$ streams (also called $C_4$ fractions) are obtained in a number of petrochemical processes, see N. Calamur, et al., "Butylenes," in *Kirk-Othmer Encyclopedia of Chemical Technology*, online edition, 2007. For example, steam cracking of hydrocarbons is widely used to produce olefins such as ethylene, propylene, butenes (1-butene, cis- and trans-2-butenes, isobutene), butadiene, and aromatics such as benzene, toluene, and xylene. In an olefin plant, a hydrocarbon feedstock such as naphtha, gas oil, or other fractions of whole crude oil is mixed with steam. This mixture, after preheating, is subjected to severe thermal cracking at elevated temperatures (800° C. to 850° C.) in a pyrolysis furnace. The cracked effluent from the pyrolysis furnace contains gaseous hydrocarbons of great variety (from 1 to 35 carbon atoms per molecule). This effluent contains hydrocarbons that are aliphatic, aromatic, saturated, and unsaturated, and may contain significant amounts of molecular hydrogen. The cracked product of a pyrolysis furnace is then further processed in the olefin plant to produce, as products of the plant, various individual product streams such as hydrogen, ethylene, propylene, mixed hydrocarbons having four or five carbon atoms per molecule (crude $C_4$'s and $C_5$'s), and pyrolysis gasoline.

Crude $C_4$'s can contain varying amounts of n-butane, isobutane, 1-butene, 2-butene (cis- and/or trans-), isobutene (isobutylene), acetylenes (ethyl acetylene and vinyl acetylene), and butadiene. The term 2-butene as used herein includes cis-2-butene, trans-2-butene, or a mixture of both.

Crude $C_4$'s are typically subjected to butadiene extraction or butadiene selective hydrogenation to remove most, if not essentially all, of the butadiene and acetylenes present. Thereafter the $C_4$ raffinate (called raffinate-1) is subjected to a chemical reaction (e.g., etherification, hydration, dimerization) wherein the isobutylene is converted to other compounds (e.g., methyl tertiary butyl ether, tertiary butyl alcohol, diisobutylene) (see, e.g., U.S. Pat. Nos. 6,586,649 and 4,242,530). The remaining $C_4$ stream containing mainly n-butane isobutane, 1-butene and 2-butene is called raffinate-2. Such a stream may react with an isomerization catalyst to produce an isomerized stream with enriched 2-butene as a result of the isomerization of 1-butene. The isomerized butenes stream may further react with ethylene to produce propylene through a so-called metathesis reaction (U.S. Pat. Nos. 5,300,718 and 5,898,091; *Appl. Ind. Catal.* 3 (1984) 215). One drawback of the process is that the presence of the paraffins (n-butane and isobutane) in the streams limits the catalyst productivity and the throughput of the plant.

It is known that paraffins can be separated from the butenes (1-butene and 2-butene) by extractive distillation or other techniques, see U.S. Pat. Nos. 4,515,661, 5,288,370, U.S. Pat. Appl. Pub. No. 2005/0154246, and DeRosset, A. J., et al., *Prepr. —Am. Chem. Soc., Div. Pet. Chem.* 23(2) (1978) 766. It would be desirable to remove the paraffins from a feed stream such as a raffinate-2 before the isomerization and the metathesis reaction. Such a paraffins-removal step would significantly increase the throughput of the plant.

SUMMARY OF THE INVENTION

The invention is a process for producing propylene. A butenes stream (1-butene and 2-butene) is produced from a feed stream comprising 1-butene, 2-butene, n-butane, and isobutane by removing the paraffins. The butenes stream is reacted in the presence of an isomerization catalyst to produce an isomerized stream with increased concentration of 2-butene. The isomerized stream is reacted with ethylene in the presence of a metathesis catalyst to produce a reaction mixture comprising propylene. The removal of paraffins from the feed stream can significantly increase the plant throughput.

DETAILED DESCRIPTION OF THE INVENTION

Figure 1:
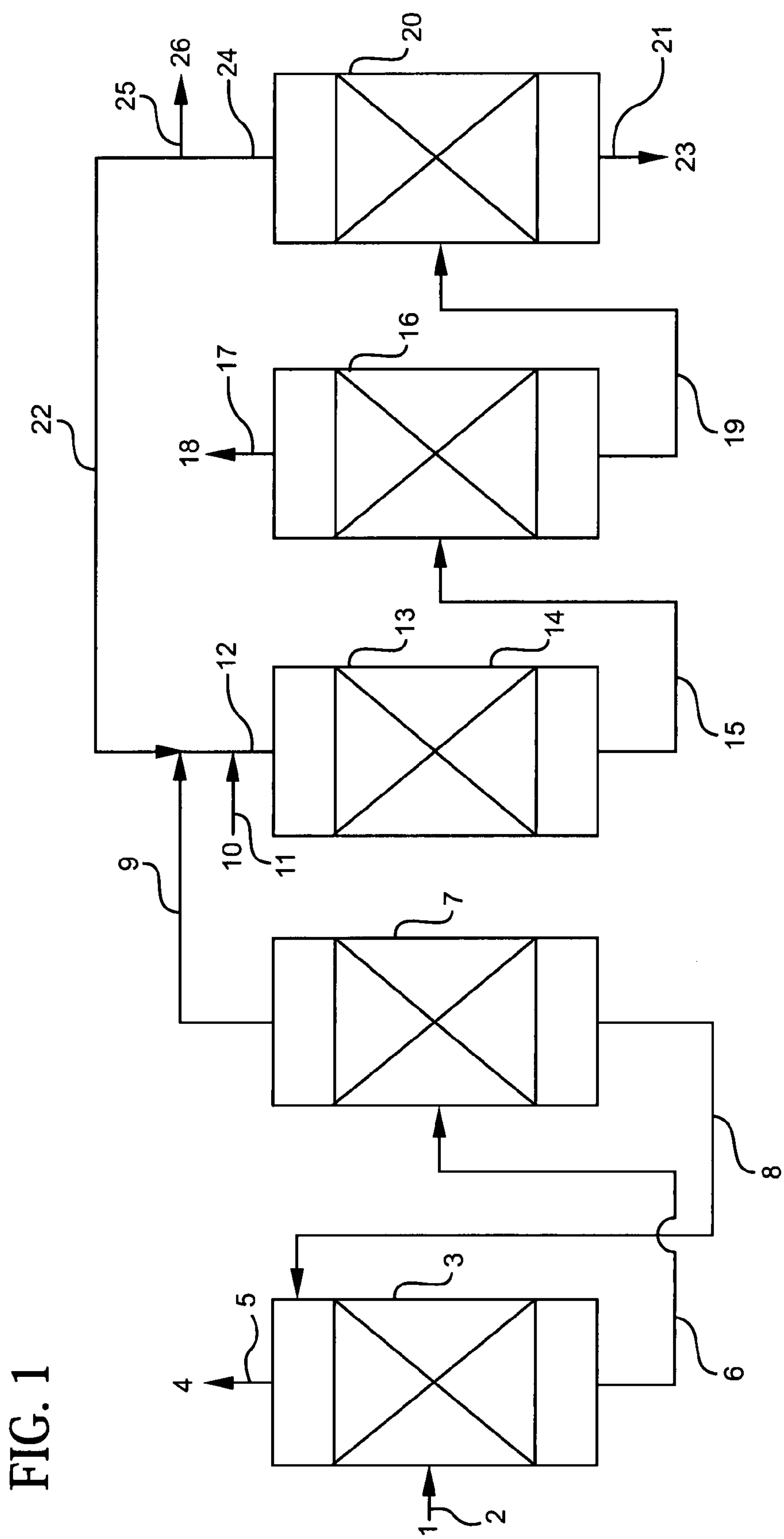
FIG. 1 is a schematic flow diagram of one embodiment of the invention.

The process of the invention comprises: (a) separating a feed stream comprising 1-butene, 2-butene, n-butane, and isobutane into a paraffins stream and a butenes stream; (b) reacting the butenes stream in the presence of an isomerization catalyst to produce an isomerized stream with increased concentration of 2-butene; and (c) reacting the isomerized stream with ethylene in the presence of a metathesis catalyst to produce a reaction mixture comprising propylene.

Any feed stream comprising 1-butene, 2-butene, n-butane, and isobutane may be used. One suitable feed stream is called raffinate-2, which is obtained from a crude $C_4$ stream from refining or steam cracking processes. Raffinate-2 contains mostly 1-butene, 2-butene, n-butane, and isobutane. Another suitable feed stream is a condensate from a Fisher-Tropsch process obtained by reacting a synthesis gas, a mixture of carbon monoxide and hydrogen, over a Fisher-Tropsch catalyst (*Catal. Lett.* 7(1-4) (1990) 317). The condensate typically contains ethylene, propylene, $C_4$ olefins, and $C_5$ and higher olefins. When a Fischer-Tropsch-derived feed is used, it may be fractionated to remove $C_5$ and higher hydrocarbons by distillation or other methods (see, e.g., U.S. Pat. No. 6,586,649).

The process comprises separating the feed stream into a paraffins stream and a butenes stream. Preferably, paraffins are removed from the feed stream by extractive distillation with a suitable solvent (e.g., acetonitrile, methyl formamide, dimethyl formamide, N-methyl-2-pyrrolidone, N-formyl morpholine, or mixtures thereof). See U.S. Pat. Nos. 4,515,661, 5,288,370, and U.S. Pat. Appl. Pub. No. 2005/0154246.

One suitable extractive distillation method is described in U.S. Pat. Appl. Pub. No. 2005/0154246. A feed stream containing 1-butene, 2-butene, n-butane and isobutane is subjected to distillation in an absorber by feeding the feed stream in gaseous or liquid form and feeding an extractive solvent in liquid form above the point where the feed stream enters the absorber. Through the countercurrent contact of the feed stream and the solvent, the feed stream is separated into a top stream comprising the paraffins, i.e., the components for which the selective solvent has lower affinities, and a bottom stream which comprises the solvent laden with components for which the extractive solvent has higher affinities than for the butanes, predominantly butenes. Preferably the feed stream is fed in gaseous form at the mid point of the absorber. There are no restrictions regarding the internals which can be used in the absorber. It is possible to use trays, random packing or structured packing. The column advantageously has from 10 to 120, preferably from 50 to 100, theoretical stages. A small amount of extractive solvent (preferably less than 1 wt. % of the total weight of the top stream) may be present in the top stream, which may be removed from the stream in a subsequent water wash step.

The pressure in the absorber is dependent on the temperature of the cooling medium in the condenser at the top of the column (well water, river water, seawater, refrigerant such as liquid propylene, liquid ammonia or brine). It is generally at a pressure of from 20 to 200 psig, frequently from 50 to 100 psig. The temperature in the column is, on the basis of the abovementioned pressure values, set so as to give suitable thermodynamic conditions under is which the extractive solvent becomes laden with butenes while the butanes in the feed stream remain in the gas phase. The temperature at the top of the column is typically in the range of from 90 to 140° F. The temperature at the bottom is typically in the range of from 150 to 250° F.

The bottom stream from the absorber is separated in a stripper at a higher temperature and if appropriate lower pressure compared to the absorber into a top stream (butenes stream) comprising the butenes and small amount of other hydrocarbons and a bottom stream comprising the extractive solvent. Suitable temperatures for the stripper are in the range of from 90 to 300° F. The recovered extractive solvent is recycled to the absorber.

Preferably, the butenes stream is primarily composed of 1-butene and 2-butene. For example, the amount of 1-butene and 2-butene combined in the butenes stream is desirably at least 95 weight percent (wt. %), more desirably at least 99 wt. %. The amount of butanes in the butenes stream is generally less than 5 wt. %, preferably less than 1 wt. %. The relative amount of 1-butene and 2-butene in the butenes stream is not critical.

The butenes stream is reacted in the presence of an isomerization catalyst to produce an isomerized stream. At least a portion of 1-butene in the feed stream is converted to 2-butene. The relative molar ratio of 1-butene to 2-butene in the isomerized stream is preferably in the range of 9:1 to 1:9. More preferably, the ratio is in the range of 1:1 to 1:5.

Many isomerization catalysts can be used, including acidic catalysts, basic catalysts, and hydroisomerization catalysts. Suitable acidic catalysts include acidic ion-exchange resins such as sulfonated resins (see, e.g., U.S. Pat. No. 3,326,866), organosulfonic acids, phosphoric acid, carboxylic acids, metal oxides (alumina, zirconia, sulfated zirconia), mixed oxides (e.g., silica-aluminas, zirconia-silicas), acidic zeolites, acidic clays (see, e.g., U.S. Pat. No. 4,992,613, U.S. Pat. Appl. Pub. Nos. 2004/249229, 2006/084831). Acidic ion-exchange resins are preferred.

When an acidic catalyst is used, the isomerization is typically conducted at a temperature of from 100 to 400° F., preferably from 190 to 300° F., and under a pressure of from 100 to 600 psig, preferably from 200 to 450 psig. The weight hourly space velocities (WHSV) are generally maintained at 0.2 to 4 $h^{-1}$.

The basic isomerization catalysts are preferably metal oxides such as magnesium oxide (magnesia), calcium oxide, barium oxide, and lithium oxide. Metal oxides supported on a carrier may be used. Suitable carriers include silicas, aluminas, titanias, silica/aluminas, and the like, and mixtures thereof (see, e.g., U.S. Pat. Nos. 5,153,165, 5,300,718, 5,120,894, 4,992,612, U.S. Pat. Appl. Pub. No. 2003/0004385). A particularly preferred basic isomerization catalyst is magnesium oxide. Suitable magnesium oxide has a surface area of at least 1 $m^2/g$, preferably at least 5 $m^2/g$. The magnesium oxide is preferably activated in a suitable manner, for example, by heating in a flowing stream of an oxygen-containing gas for about 0.5 to about 30 h at 450 to 1500° F., preferably at 600 to 1200° F. before use.

Isomerization in the presence of a magnesium oxide catalyst may be conducted at a temperature ranging from 120 to 950° F., preferably ranging from 300 to 900° F., most preferably ranging from 500 to 700° F. The reaction is preferably conducted at a pressure in the range of from 250 to 500 psig with a WHSV of from 0.2 to 4 $h^{-1}$.

The isomerization of the butenes stream may be catalyzed by a hydroisomerization catalyst in the presence of small amount of hydrogen. Hydroisomerization reaction of olefins is well known (*Hydrocarbon Process., Int. Ed*. May 1979, 112). Suitable catalysts include supported noble metal catalysts (e.g., Pd or Pt supported on silica or alumina, see U.S. Pat. No. 3,531,545). A catalyst comprising Pd and alumina is preferred. The hydrogen to hydrocarbon feed molar ratio is typically in the range of 1:10 to 1:100. The hydroisomerization is usually conducted at a temperature of from 90 to 300° F., preferably 100 to 200° F., and under a pressure of from 75 to 300 psig, preferably from 100 to 200 psig. The weight hourly space velocity may be maintained at 0.1 to 20, preferably 1 to 10 $h^{-1}$.

The hydroisomerization of the butenes stream is particularly preferred if the butenes stream contains small amount of butadiene or acetylenes. A hydroisomerization process not only converts 1-butene to 2-butene, it also converts butadiene or $C_4$-acetylenes to 1-butene and 2-butene.

The isomerization catalysts are preferably in the form of beads, granules, pellets, extrudates, tablets, agglomerates, and the like. The catalyst is preferably used in a fixed bed and the reaction is performed in a continuous flow mode.

The isomerized stream is reacted with ethylene in the presence of a metathesis catalyst to form a reaction mixture comprising ethylene, propylene, 1-butene 2-butene, and $C_5$ and higher olefins. Metathesis catalysts are well known in the art (see, e.g., *Appl. Ind. Catal*. 3 (1984) 215). Typically, the metathesis catalyst comprises a transition metal oxide. Suitable transition metal oxides include oxides of cobalt, molybdenum, rhenium, tungsten, and mixtures thereof. Conveniently, the catalyst is supported on a carrier. Suitable carriers include silicas, aluminas, titanias, zirconias, zeolites, clays, and mixtures thereof. Silicas and aluminas are preferred. The catalyst may be supported on a carrier in any convenient fashion, in particular by adsorption, ion-exchange, impregnation, precipitation, or sublimation. The transition metal oxide constituent of the catalyst may amount to 1 to 30 wt. % of the total catalyst, preferably 5 to 20 wt. %. A catalyst comprising tungsten oxide and silica is particularly suitable for the present invention (see, e.g., U.S. Pat. No. 5,120,894).

The preferred metathesis catalysts are in the form of particulates. The catalyst particles such as beads, granules, pellets, extrudates, tablets, agglomerates, honeycomb monolith, and the like are sufficiently large so as not to cause high pressure drops through the catalyst bed.

The operating temperature for the metathesis reaction is generally in the range of about 300 to 1200° F., preferably in the range of 500 to 850° F. The pressures are not that critical but will be in the range of about 0 to 2,500 psig, preferably in the range of 300 to 800 psig. An ethylene to butenes mole ratio of from 0.5:1 to 3:1 can be employed, typically 0.8:1 to 2:1. Weight hourly space velocity based on hydrocarbons and total weight of metathesis catalyst including catalyst carrier is generally in the range of from 5 to 50 $h^{-1}$, preferably in the range of 10 to 25 $h^{-1}$.

Preferably, the isomerized stream is treated with an adsorption bed to remove impurities to extend the metathesis catalyst life (see U.S. Pat. No. 5,120,894). The purity of the isomerized stream is an important factor in the process since it affects directly the efficiency or even operability of the process. Olefin metathesis processes in general require the substantial absence of impurities which can deactivate the catalyst. Some of these impurities are, e.g., water, alcohols, aldehydes, ketones, ethers, carboxylic acids, carboxylic esters, sulfur-containing compounds, and nitrogen-containing compounds. Many adsorbents may be used such as silicas, aluminas, zeolites, clays, etc. Alumina is particularly preferred. The contact with the adsorbent can be either in vapor or liquid phase, but is preferably in liquid phase.

In one preferred embodiment of the invention, the isomerization and metathesis reactions are carried out in the same reactor. Thus a mixed bed of isomerization catalyst and metathesis catalyst is used; and the butenes stream and ethylene are fed to the reactor. Although other isomerization catalysts and metathesis catalysts may be used, a combination of magnesium oxide and tungsten oxide-on-silica is particularly preferred. When preparing a mixed catalyst, particles of magnesium oxide and particles of the tungsten oxide-on-silica of about the same size can be blended. Alternatively, both magnesium oxide and the tungsten oxide-on-silica catalyst can be intimately blended by crushing, grinding, milling, and the like. The powder then is formed into other shapes such as pellets, tablets, agglomerates, extrudates, and the like, so that each particle comprises an intimate blend of the two catalysts. The proportion of magnesium oxide to the tungsten oxide-on-silica in the mixed catalyst can vary widely. The weight ratio of magnesium oxide to tungsten oxide is typically in the range of from 1:10 to 10:1, preferably from 1:1 to 5:1.

The catalyst bed is preferably configured so that the upstream end of the bed contains the isomerization catalyst only and the downstream end of the bed contains a mixture of the isomerization catalyst and the metathesis catalyst. In this case, the reactor itself is preferably a down-flow unit, and the catalyst is layered so that the concentration of metathesis catalyst increases toward the downstream end of the bed. For example, when magnesium oxide and tungsten oxide-on-silica are used, the magnesium oxide to tungsten oxide ratio decreases from upstream to downstream through the bed.

The reaction with magnesium oxide and tungsten oxide-on-silica mixed catalyst bed may be carried out at a temperature of from 500 to 800° F., preferably at 600 to 700° F., and at a pressure of 0 to 2,500 psig, preferably 0 to 800 psig, more preferably 200 to 600 psig, and at a WHSV of from 0.01 to 1,000 $h^{-1}$, more preferably from 5 to 50 $h^{-1}$.

A deactivated mixed catalyst bed containing magnesium oxide and tungsten oxide-on-silica may be regenerated at a temperature in the range of 400 to 700° C., preferably in the range of 500 to 600° C. with an oxygen-containing atmosphere with an oxygen content of 1 to 20 mole %, preferably between 2 to 10 mole %.

When the isomerization and metathesis reactions are carried out in the same reactor, the butenes stream and ethylene are preferably treated with an adsorption bed as described above to remove impurities from the feed.

The reaction mixture from the metathesis reaction (or from the isomerization/metathesis reactions in the case of using a mixed catalyst) contains ethylene, propylene, 1-butene, 2-butene, and $C_5$ and higher olefins. The reaction mixture may be separated using standard distillations. For example, propylene and ethylene can be collected as an overhead, which may be further separated by standard techniques into ethylene and propylene. The further-separated ethylene stream may be recycled to the metathesis reactor of step (c). The bottoms stream comprising 1-butene, 2-butene, and $C_5$ and higher olefins may be further distilled to separate 1-butene and 2-butene as a light stream, while the $C_5$ and higher olefins is taken as a heavy stream. The light stream is preferably recycled to the isomerization step (b).

The following Example illustrates the invention.

EXAMPLE

In the scheme in FIG. 1, acetonitrile (ACN) is used as an extractive solvent. The solvent enables $C_4$ paraffins to be separated as lights from $C_4$ olefins.

Unit 3 is an extractive distillation absorber. It contains 100 ideal stages. The overhead pressure is 65 psig and the bottoms pressure is 75 psig. The reflux ratio is 6:1 by weight. The overhead temperature is 113° F. and the bottoms temperature is 198° F. The feed stream 1 enters unit 3 at stage 50 at 134° F. The expected flows of streams and their compositions are shown in Table 1. $C_4$ paraffins stream 4 is removed as overhead (distillate) from this tower. A small amount of ACN is lost in the overhead stream 4, which is removed via a water wash step (not shown).

Unit 7 is an extractive distillation stripper. This tower contains 30 ideal stages. The bottoms stream from unit 3 enters unit 7 through line 6 at stage 15 of tower 7. The overhead pressure is 65 psig and the bottoms pressure is 70 psig. The reflux ratio is 5:1 by weight. The overhead temperature is 107° F. and the bottoms temperature is 285° F. A small amount of fresh ACN is added to the bottoms of this tower to make up for the amount lost in the overhead stream of the unit 3.

Unit 13 is an isomerization/metathesis reactor. It contains a mixture of $WO_3$-on-silica and MgO (both having an average particle diameter of 4 mm) at the weight ratio of 1:3. The feed enters reactor 13 through line 12 at 650° F. Ethylene is fed to unit 13 through line 10. The inlet pressure is 460 psig. The WHSV based on $C_4$ feed relative to $WO_3$-on-silica catalyst is 15 $h^{-1}$. This reactor converts $C_4$ olefins and ethylene to produce propylene and minor amounts of $C_5$ and higher olefins.

Unit 16 is a distillation tower where ethylene and propylene are recovered from the product stream of reactor 13. The tower contains 40 ideal stages and the feed entered on stage 20 through line 15. Ethylene and propylene are recovered as overhead stream 18. The ethylene is recovered and recycled (not shown) back to isomerization/metathesis reactor 13. The pressure of the tower is 400 psig at the top and 410 psig at the bottom. The reflux ratio is 2:1 by weight. The overhead temperature is 74° F. and the bottoms temperature is 276° F.

Unit 20 is a distillation tower where unreacted $C_4$'s are separated as overhead stream entering line 24. The tower contains 30 ideal stages with the feed entering on stage 15. The top of the tower is at 100 psig and the bottom at 105 psig. The tower overhead temperature is 140° F. and the bottoms temperature is 235° F. The reflux ratio of this tower is 3:1 by weight. Majority of the stream (about 90%) in line 24 is recycled to unit 13 through line 22. $C_5$ and higher hydrocarbons (bottoms stream 23) are removed through line 21. A portion of the tower overhead (about 10%) is purged to remove $C_4$ paraffins as stream 26 through line 25. The calculated flow rates of different components in various lines are listed in Table 1.

In FIG. 1, the removal of paraffins from the feed stream enables the significantly increased propylene production. If paraffins in the feed stream were is not removed, they build up in stream 22 (see FIG. 1) and effectively prevent $C_4$'s from being recycled back to the isomerization/metathesis reactor 13. The present invention increases the productivity of the isomerization/metathesis reactor and makes the recycling of the unreacted $C_4$ stream (stream 22 in FIG. 1) practical.

TABLE 1

| Flow Rates of Streams (lb/h) | | | | | | | | | | |
|---|---|---|---|---|---|---|---|---|---|---|
| | Stream | | | | | | | | | |
| | 2 | 5 | 8 | 9 | 22 | 11 | 15 | 17 | 21 | 26 |
| Ethylene | | | | | | 11538 | 7723 | 7723 | | |
| Propylene | | | | | | | 11141 | 11141 | | |
| Cis-2-butene | 1500 | | | 1500 | 1000 | | 1100 | | | 100 |
| Trans-2-butene | 1625 | | 0.02 | 1625 | 1123 | | 1247 | | | 124 |
| 1-Butene | 4875 | 135 | | 4740 | 595 | | 661 | | | 66 |
| Isobutene | 250 | | | 250 | 705 | | 783 | | | 78 |
| $C_4$ paraffins | 4250 | 4184 | | 66 | 594 | | 660 | | | 66 |
| $C_5$ olefins | | | | | | | 380 | | 380 | |
| $C_6$ olefins | | | | | | | 41 | | 41 | |
| Acetonitrile | | 98 | 60000 | | | | | | | |
| Total | 12500 | 4417 | 60000 | 8181 | 4017 | 11538 | 23736 | 18864 | 421 | 434 |

I claim:

1. A process for producing propylene comprising:

(a) separating a feed stream comprising 1-butene, 2-butene, n-butane, and isobutane into a paraffins stream and a butenes stream;

(b) reacting the butenes stream in the presence of an isomerization catalyst to produce an isomerized stream with increased concentration of 2-butene and having less than 5 wt. % butanes;

(c) reacting the isomerized stream having less than 5 wt. % butanes and ethylene in the presence of a metathesis catalyst to produce a reaction mixture comprising propylene, (d) distilling the reaction mixture to separate an ethylene stream, a propylene stream, and a bottoms stream comprising 1-butene, 2-butenes, and C5 and higher olefins;

(e) distilling the bottoms stream to produce a light stream comprising 1-butene and 2-butenes and a heavy stream comprising C5 and higher olefins; and (f) recycling at least a portion of the light stream to step (b), wherein the butenes stream comprises butanes in an amount of less than 5 wt. %.

2. The process of claim 1 wherein step (a) is carried out by extractive distillation with a solvent.

3. The process of claim 2 wherein the solvent is selected from the group consisting of acetonitrile, methyl formamide, dimethyl formamide, N-methyl pyrrolidone, N-formyl morpholine, and mixtures thereof.

4. The process of claim 1 wherein 1-butene and 2-butene constitute at least 95 wt. % of the butenes stream.

5. The process of claim 1 wherein 1-butene and 2-butene constitute at least 99 wt. % of the butenes stream.

6. The process of claim 1 wherein the isomerization catalyst is an acidic ion-exchange resin.

7. The process of claim 1 wherein the isomerization catalyst is a basic catalyst.

8. The process of claim 1 wherein the isomerization catalyst comprises magnesium oxide.

9. The process of claim 1 wherein the isomerization catalyst is a hydroisomerization catalyst.

10. The process of claim 9 wherein the hydroisomerization catalyst comprises Pd and alumina.

11. The process of claim 1 wherein the metathesis catalyst comprises a transition metal oxide comprising an element selected from the group consisting of cobalt, molybdenum, rhenium, tungsten, and mixtures thereof.

12. The process of claim 1 wherein the metathesis catalyst comprises tungsten oxide and silica.

13. The process of claim 1 wherein steps (b) and (c) are conducted in the same reactor.

14. The process of claim 13 wherein the reactor contains a mixture of a tungsten oxide-on-silica and magnesium oxide.

15. The process of claim 14 wherein steps (b) and (c) are conducted at a temperature in the range of 500 to 850° F.

16. The process of claim 14 wherein steps (b) and (c) are conducted at a pressure in the range of 300 to 800 psig.

17. The process of claim 14 wherein steps (b) and (c) are conducted in a down-flow fixed-bed reactor.

18. The process of claim 1 wherein the isomerized stream and ethylene are treated in an adsorption bed prior to step (c).

19. The process of claim 18 wherein the adsorption bed is an alumina bed.

20. The process of claim 1 wherein the amount of butanes in the butenes stream is less than 1 wt. %.

* * * * *